United States Patent
Boehm, Jr. et al.

(10) Patent No.: US 11,944,548 B2
(45) Date of Patent: Apr. 2, 2024

(54) MINIMALLY INVASIVE SURGICAL SYSTEMS FOR FUSION OF THE SACROILIAC JOINT

(71) Applicants: Frank H. Boehm, Jr., New Hartford, NY (US); Gregory B. Shankman, Clinton, NY (US)

(72) Inventors: Frank H. Boehm, Jr., New Hartford, NY (US); Gregory B. Shankman, Clinton, NY (US)

( * ) Notice: Subject to any disclaimer, the term of this patent is extended or adjusted under 35 U.S.C. 154(b) by 0 days.

(21) Appl. No.: 17/559,669

(22) Filed: Dec. 22, 2021

(65) Prior Publication Data

US 2022/0110754 A1   Apr. 14, 2022

Related U.S. Application Data (63) Continuation of application No. 16/312,866, filed as application No. PCT/US2017/039007 on Jun. 23, 2017, now abandoned.

(60) Provisional application No. 62/353,828, filed on Jun. 23, 2016.

(51) Int. Cl.
  *A61F 2/30* (2006.01)
  *A61B 17/16* (2006.01)
  *A61F 2/46* (2006.01)

(52) U.S. Cl.
  CPC .......... *A61F 2/30988* (2013.01); *A61B 17/16* (2013.01); *A61F 2002/30136* (2013.01); *A61F 2002/30995* (2013.01); *A61F 2/4603* (2013.01)

(58) Field of Classification Search
  CPC ............................................ A61F 2002/30995
  See application file for complete search history.

(56) References Cited

U.S. PATENT DOCUMENTS

| | | |
|---|---|---|
| 8,388,667 B2 | 3/2013 | Reiley et al. |
| 8,808,377 B2 | 8/2014 | Donner |
| 8,840,623 B2 | 9/2014 | Reiley |
| 9,333,090 B2 | 5/2016 | Donner et al. |
| 9,788,961 B2 | 10/2017 | Donner et al. |
| 10,426,533 B2 | 10/2019 | Mauldin et al. |
| 2008/0140200 A1 | 6/2008 | Heinz |
| 2009/0204214 A1 | 8/2009 | Fuji et al. |
| 2010/0106200 A1 | 4/2010 | Stark |
| 2010/0185292 A1 | 7/2010 | Hochschuler et al. |
| 2011/0022176 A1 | 1/2011 | Zucherman et al. |
| 2011/0184518 A1 | 7/2011 | Trieu |
| 2011/0184519 A1 | 7/2011 | Trieu |
| 2011/0264229 A1 | 10/2011 | Donner |
| 2013/0238093 A1 | 9/2013 | Mauldin et al. |

(Continued)

FOREIGN PATENT DOCUMENTS

WO   WO2012174485   12/2012

OTHER PUBLICATIONS

ISA/US; International Search Report/Written Opinion for International application PCT/US17/39007 dated Sep. 28, 2017; 10 pages.

(Continued)

*Primary Examiner* — Nicholas W Woodall
(74) *Attorney, Agent, or Firm* — Christopher E. Blank; Schmeiser, Olsen & Watts, LLP (57) ABSTRACT

A sacroiliac fusion stabilizer (SIFS) for fusing a first bone fracture fragment to a second bone fracture fragment is provided. In one embodiment, the SIFS has a lazy-S shape with a series of protrusions at the ends of the SIFS. In another embodiment, the SIFS has two overlapping lazy-S shapes.

7 Claims, 10 Drawing Sheets

(56) References Cited

U.S. PATENT DOCUMENTS

2015/0250595 A1  9/2015  Mauldin et al.
2016/0081809 A1  3/2016  Schneider et al.
2016/0081810 A1  3/2016  Reiley et al.

OTHER PUBLICATIONS

EPO; European Search Report dated May 8, 2020 issued in corresponding EP Application 17816297.0; 7 pages.

MINIMALLY INVASIVE SURGICAL SYSTEMS FOR FUSION OF THE SACROILIAC JOINT

CROSS-REFERENCE TO RELATED APPLICATIONS

This application claims priority to and is a Continuation-in-Part of U.S. patent application Ser. No. 16/312,866 (filed Dec. 21, 2018) which is a US National Stage Application of PCT/US2017/039007 (filed Jun. 23, 2017) which claims priority to U.S. Provisional Application 62/353,828 (filed Jun. 23, 2016), the entirety of which is incorporated herein by reference.

BACKGROUND OF THE INVENTION

Many causes of lower back pain have been identified, and the differential diagnosis of low back pain is indeed foreboding when first reviewed. However, most causes can be identified by other associated symptoms and the vast majority of patients with lower back pain are found to have degenerative disease of the spine. More recently, a study performed at the National Institute of Health (NIH) in Bethesda, MD, has shown that upwards of 20% of patients with chronic low back pain actually suffer from inflammation/irritation of one or both of the sacroiliac joints. These are the junctions between the sacrum, which is the base of the spine, and the posterior-medial aspect of the iliac bones. Treatment of pain arising from the sacroiliac joint (SIJ) is usually managed with measures such as chiropractic adjustments, massage, anti-inflammatory medications, and local injections. However, there are a number of patients who do not respond well to these measures, or in whom the response to other measures was merely transient, and in this setting fusion of the lumbar spine is often considered. This is somewhat controversial; detractors of the procedure point to the fact that this joint is a fixed joint to begin with, and as such there is little movement naturally occurring. Proponents suggest that even a minute amount of movement can cause symptoms, and point to the fact that this procedure was first performed many years ago and has been reliably performed since then with reasonable success. Fusion seems to resolve sacroiliac joint pain syndromes with a fairly high rate of success.

A common scenario for SIJ pain syndromes is in the post lumbar fusion patient, particularly patients who have undergone fusion of the L5-S1 segment. Such individuals have had motion eliminated at L5-S1 and are now believed to be passing increased stress along to the SIJ, much the same way that the so-called "adjacent disc disease" inflicts its pathophysiology. Such patients may be candidates for SIJ fusion.

The discussion above is merely provided for general background information and is not intended to be used as an aid in determining the scope of the claimed subject matter.

BRIEF DESCRIPTION OF THE INVENTION

In a first embodiment, a sacroiliac fusion stabilizer (SIFS) for fusing a first bone fracture fragment to a second bone fracture fragment is provided. The SIFS comprising: a first lateral surface having a first curvature; a second lateral surface, opposite the first lateral surface, having a second curvature; the first lateral surface being spaced from the second lateral surface by a depth that defines a first side and a second side; a cannulation that extends from the first side, through the SIFS and terminates at the second side; and the first curvature and the second curvature providing a lazy-S shape such that the first lateral surface contacts the second lateral surface at a first junction and a second junction, the first junction being disposed proximate the first lateral surface and the second junction being disposed proximate the second lateral surface.

In a second embodiment, a sacroiliac fusion stabilizer (SIFS) for fusing a first bone fracture fragment to a second bone fracture fragment is provided. The SIFS comprising at least a first arm and a second arm defined by: a first lateral surface having a first curvature; a second lateral surface, opposite the first lateral surface, having a second curvature; the first lateral surface being spaced from the second lateral surface by a depth that defines a first side and a second side; a cannulation that extends from the first side, through the SIFS and terminates at the second side; the first curvature and the second curvature providing a lazy-S shape such that the first lateral surface contacts the second lateral surface at a first junction and a second junction, the first junction being disposed proximate the first lateral surface to form the first arm and the second junction being disposed proximate the second lateral surface to form the second arm; the first junction providing a first plurality of projections, and the second junction providing a second plurality of projections, wherein each projection in the first plurality of projections is spaced from a first lateral line by a first distance that is unique within the first plurality of projections: each projection in the second plurality of projections is spaced from a second lateral line by a second distance that is unique within the second plurality of projections.

In a third embodiment, a sacroiliac fusion stabilizer (SIFS) for fusing a first bone fracture fragment to a second bone fracture fragment is provided. The SIFS comprising at least a first arm and a second arm defined by: a first lateral surface having a first curvature; a second lateral surface, opposite the first lateral surface, having a second curvature; the first lateral surface being spaced from the second lateral surface by a depth that defines a first side and a second side; a cannulation that extends from the first side, through the SIFS and terminates at the second side; the first curvature and the second curvature providing a lazy-S shape such that the first lateral surface contacts the second lateral surface at a first junction and a second junction, the first junction being disposed proximate the first lateral surface to form the first arm and the second junction being disposed proximate the second lateral surface to form the second arm; the first junction providing a first plurality of projections, and the second junction providing a second plurality of projections, wherein each projection in the first plurality of projections is spaced from a first lateral line by a first distance that is unique within the first plurality of projections; each projection in the second plurality of projections is spaced from a second lateral line by a second distance that is unique within the second plurality of projections; and a first plurality of fenestrations in the first lateral surface and a second plurality of fenestrations in the second lateral surface.

This brief description of the invention is intended only to provide a brief overview of subject matter disclosed herein according to one or more illustrative embodiments and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This disclosure relates to the general field of spinal surgery and specifically to a device and method for use by which a surgeon can stabilize and fuse the sacroiliac joint using a minimally invasive technique. The same technique can be applied to sites of non-healing fractures at other sites. The disclosed device and method fuses the sacroiliac joint using a minimally invasive technique. Once the joint is identified, a guide needle is passed into the joint and the position of the needle is confirmed. A cannulated drill is then disposed over the needle, and advanced until the drill is at the level of the joint. The drill is then activated and a receiving bed is cored out. A sacroiliac fusion stabilizer (SIFS) is then disposed over the needle and passed into the joint at the level of the receiving bed. The SIFS is then rotated a partial turn and projections of the SIFS engage the bone and lock the SIFS into position. The SIFS is then filled with bone fusion substrate. The SIFS can also be utilized in the setting of non-healing fractures at other sites. A more detailed description follows.

Figure 1:
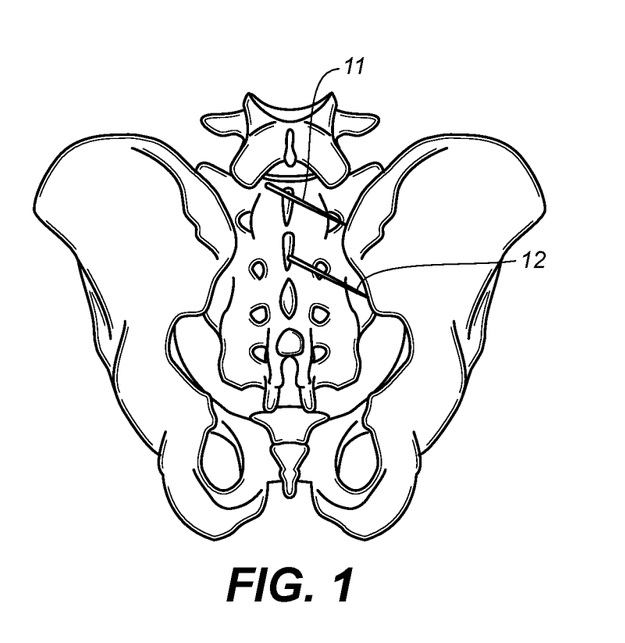
FIG. 1 is a posterior view of a right sacroiliac joint with guide needles in position.

The SIFS is implanted into the sacroiliac joint to provide stabilization and promote fusion. In FIG. 1, a posterior view of the right sacroiliac joint is shown. Superior guide needle 11 and inferior guide needle 12 have been inserted into respective target joint spaces. This may be done under radiological guidance. For example, the procedure may be performed under X-rays, CAT scanning, MRI scanning, or any other acceptable imaging techniques. The sacroiliac joint is then identified.

Figure 2:
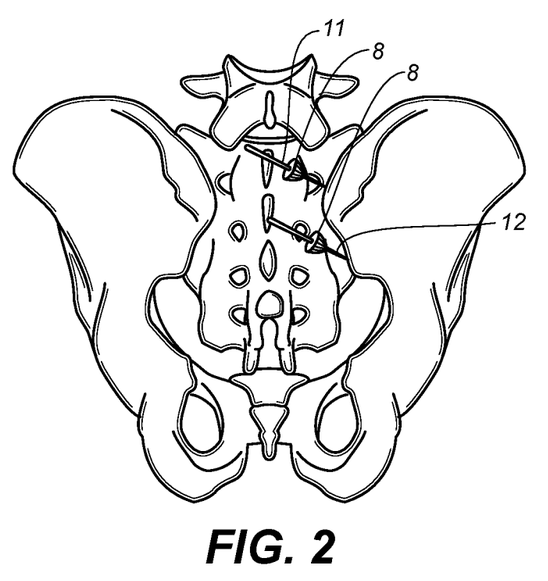
FIG. 2 depicts a cannulated drill being disposed over the guide needle.
Figure 3:
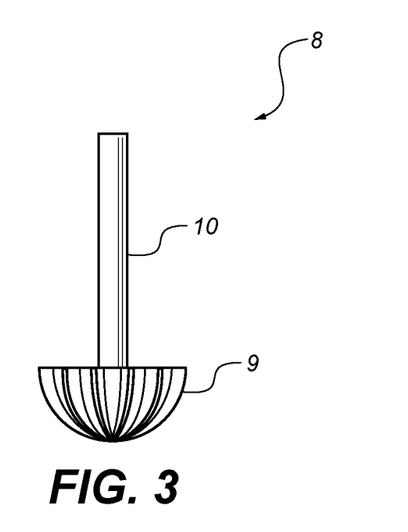
FIG. 3 is a lateral view of a cannulated drill.
Figure 4:
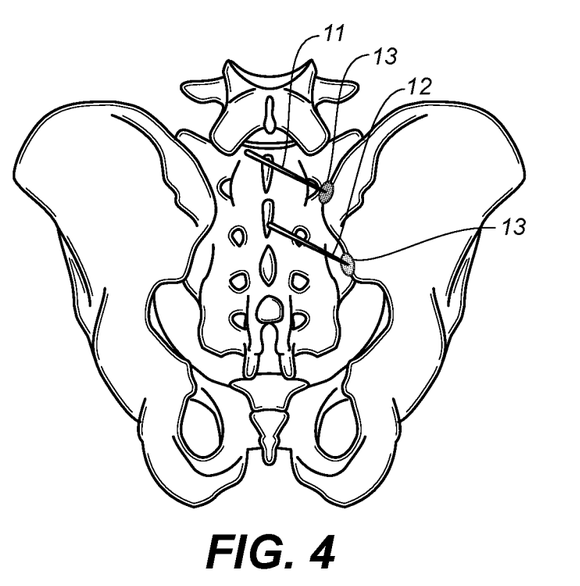
FIG. 4 shows a receiving bed formed in the right sacroiliac joint.

A cannulated drill is disposed over the superior guide needle 11 and inferior guide needle 12 and cores out a receiving bed for the SIFS. This can be seen in FIG. 2, in which a cannulated drill 8 is passing over both the superior guide needle 11 and inferior guide needle 12. A lateral view of one cannulated drill 8 is provided in FIG. 3. The cannulated drill 8 is provided with a leading end 9 which provides a cutting blade of the cannulated drill 8. A shaft 10 is connected to either a manual actuator or a power-driven actuator which is powered by a pneumatic, electric, or other power source which is known in the art. In this fashion, a receiving bed 13 is cored out for implantation of the SIFS as shown in FIG. 4. The receiving bed 13 is seen centered over the sacroiliac joint. The receiving bed 13 is coextensive with both the sacrum and the ilium thus encouraging fusion of the SU.

In one embodiment, the SIFS is positioned initially with the long axis of the SIFS being parallel to the long axis of the SU. The SIFS is then rotated a quarter of a turn, at which point projections engage the bone of the sacrum and the ilium, thus bridging the joint and promoting fusion. Additional bone can be packed around the SIFS. Other media, such as BMP, can be utilized instead of the additional bone.

A similar procedure is utilized when implanting the SIFS into the site of a fracture with a non-union. The non-union would be radiographically identified, and after anesthesia is established, a needle would be passed into the site of the non-union. Then a small incision would be accomplished, and the drill is disposed over the non-union. At that point, the SIFS is filled with bone and implanted using the technique described above. The SIFS is disposed over the guide needle and rotated approximately one-quarter turn (90°) to lock projections at the lateral ends of the SIFS into the bone of the receiving bed. Additional bone can be packed around the SIFS.

Figure 5A:
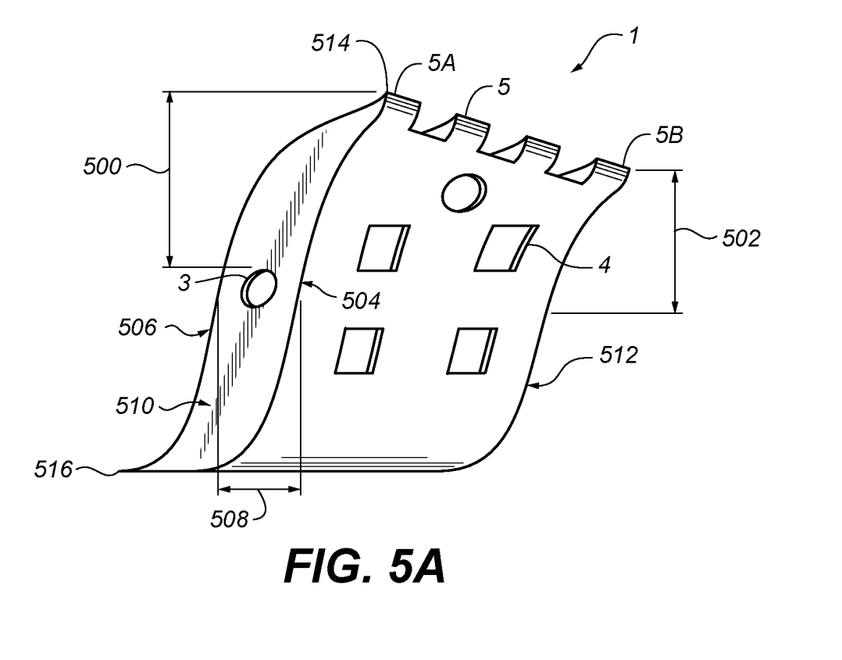
FIG. 5A is an elevational perspective view of one embodiment of the sacroiliac fusion stabilizer (SIFS)

FIG. 5A depicts an elevational perspective view a SIFS 1. Features noted include the "lazy S" configuration of the body, as well as the cannulation 3 which permits the SIFS 1 to be disposed over a guide needle. Multiple fenestrations 4 are seen in the frame of the SIFS 1 and these are deigned to permit bony growth to be incorporated through the body of the SIFS 1. A leading end of the SIFS 1 has been provided with multiple projections 5 which engages the bone, stabilizes the construct and promotes bony growth. The large surface area of the SIFS 1 encourages increased bone growth in the area.

The SIFS 501 has a first lateral surface 504 and a second lateral surface 506 separated by a depth 508 that defines a first side 510 and a second side 512. The first lateral surface 504 and the second lateral surface 506 have curvatures that produce the lazy-S shape such that the first lateral surface 504 contacts the second lateral surface 506 at a first junction 514 and a second junction 516. The first junction 514 is proximate the first lateral surface 504 and the second junction 516 is proximate the second lateral surface 506.

In the embodiment of FIG. 5A, the SIFS 1 is multi-curvilinear in configuration, substantially configured to be shaped like a "Lazy-S" in its appearance. The SIFS 1 has a central portion, being tapered to a point along its superior and inferior edges. The central portion is provided with a central chamber which is hollow. This central chamber may be filled with fusion substrate to promote in-growth of fusion mass through the SIFS 1 and from the ilium to the sacrum. There is a leading end of the SIFS 1 as well as a trailing end. The leading end is that portion of the device which is initially placed into the receiving bed. In one embodiment, the leading end is slightly tapered in contrast to the trailing end, but any geometric configuration is within the spirit and scope of the invention. A tapered leading end is more easily implanted within a receiving bed which has been drilled out. One can, of course, also envision a somewhat cylindrical configuration composed of multiple "lazy S" configurations.

A prominent feature along the broad lateral surface of the SIFS 1 is the presence of multiple fenestrations 4, which communicate with the central chamber. Furthermore, the fenestrations 4 are present on both sides of the SIFS 1 and communicate with each other through the central channel. This presents a large surface area to the SIFS 1 and promotes bony fusion to extend through the central portion. This also promotes bony fusion in the setting of non-healing fractures.

Figure 5B:
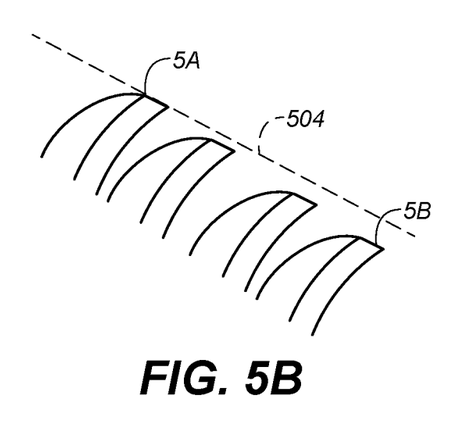
FIG. 5B is an enlarged view of projections of the SIFS.

Another prominent feature is the presence of multiple projections 5 are extending from the lateral edges of the SIFS 1. The projections 5 are slightly curved as viewed from the top view, conforming to and aligning with the curvature created by the tapered ends of the "Lazy S" configuration of the SIFS 1. These curved projections 5 designed to be implanted into a receiving bed. The projections 5 contribute significantly to the overall function and purpose of the SIFS 1. The projections 5 are somewhat eccentric in their orientation. Referring to FIG. 5A, the projections 5 include a proximate projection 5A and a distal projection 5B, with the proximate projection 5A being that end of the projections which engages the bone initially during insertional rotation. In order to engage the bone, the eccentric orientation of the projection 5 is such that the distal projection 5B is slightly closer to the cannulation 3 of the SIFS 1 while the proximate projection 5A is closer to the cannulation 3 of the SIFS 1 (distance 500 is greater than distance 502). Referring to FIG. 5B, this offsets the projections 5 from a lateral line 504 with each projection 5 being spaced from the lateral line 504 by an increasing distance. In this fashion, these projections 5 function very much the same as the threading of a screw. The function of the projections 5 is to secure the SIFS into the target area of the bone, so any embodiment of these projections which achieves that end is acceptable.

In order to favorably dispose the SIFS 1 into a receiving bed, the curved projections 5 are configured such that a concave end of the curved projections 5 is the leading end during insertional rotation. This is generally accomplished with rotation of the SIFS during insertion; hence, as viewed from the top view, this would be accomplished with rotation to the viewer's right. Therefore, again as viewed from the top view, the concave surface of the superior projection would be located on the right side of the projection and the convex surface would be on the left. This arrangement would be reversed on the inferior projection. However, other configurations of such a projection would be within the spirit and scope of this application. In one embodiment, the SIFS is positioned into the receiving bed and rotated at least one-quarter turn in order to be locked into place. It need not be rotated a great deal, such that it is not, per se, "screwed" into position. Rather, a partial turn may be utilized to promote engagement of the projections with the bone. From the leading end to the trailing end, the SIFS may be gently rotated in a clockwise or counterclockwise direction. In the embodiment of FIG. 5A, these projections 5 are of equal size. Alternatively, the projects 5 may be more robust at the trailing end of the device.

In one embodiment the SIFS is slightly larger than the receiving bed which has been drilled out. In this way, the SIFS can be secured into the bed with the projections 5 securely engaging the bone, and the SIFS being somewhat compressed in its final position. This will promote bony fusion.

Figure 6:
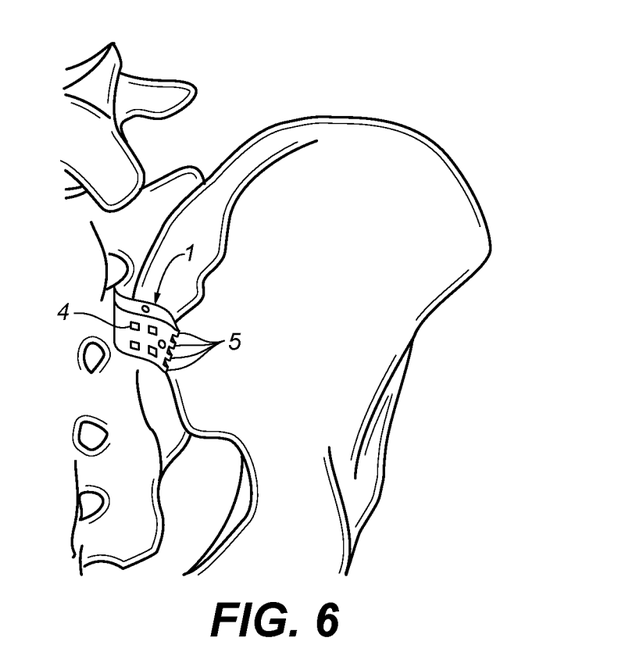
FIG. 6 shows a SIFS after implantation and rotation.
Figure 7:
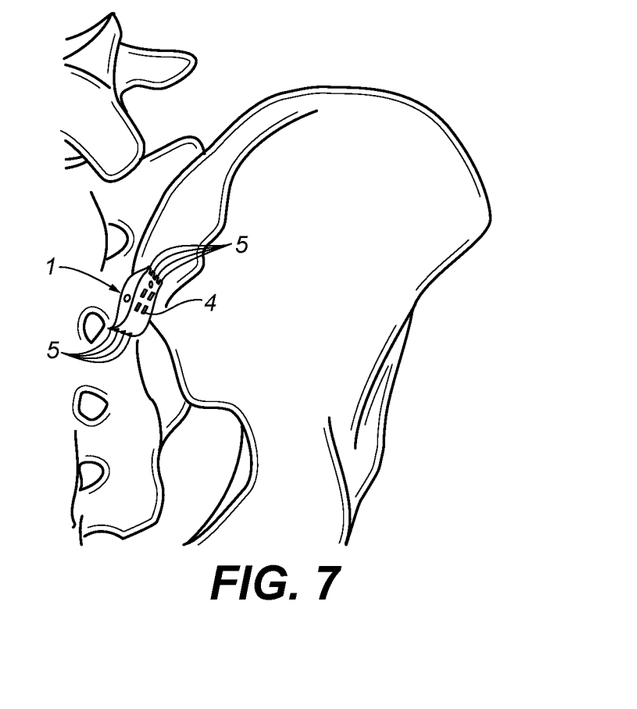
FIG. 7 depicts one embodiment of a SIFS that is oriented along the SI joint axis.

The orientation of the SIFS 1 is further demonstrated in FIG. 6, which is a close-up of the implanted SIFS 1 within the right sided sacroiliac joint. The projections 5 can be seen engaging the bone of the ilium. Fenestrations 4 in the SIFS 1 promote bone fusion. The SIFS 1 can also be oriented along the course of the sacroiliac joint as seen in FIG. 7.

Figure 8:
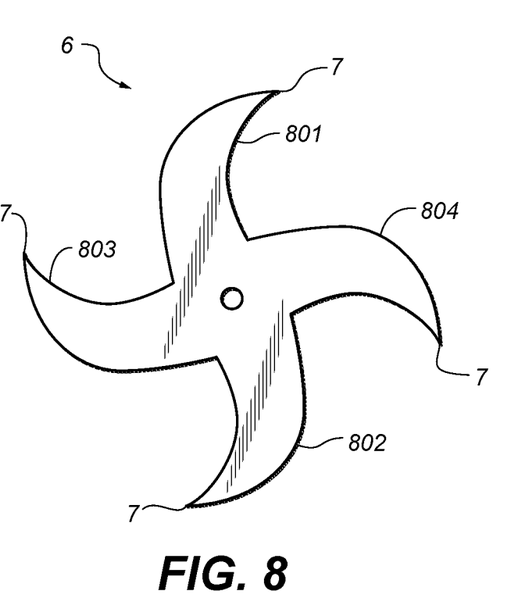
FIG. 8 is a top view of another embodiment with four arms on the SIFS.

FIG. 8 demonstrates the top view of an alternative embodiment of a SIFS 6 in which there are four arms 7 rather than two such that the overall embodiment resembles an "X shape" rather than a "Lazy S" as viewed from the top perspective. This embodiment is otherwise utilized as described elsewhere in this specification. In the embodiment of FIG. 8, the SIFS 6 comprises a first arm 801 and a second arm 802. These arms provide a lazy-S shape as described with regard to SIFS 1. Likewise, the SIFTS 6 comprises a third arm 803 and a fourth arm 804 that provides a second lazy-S shape. In this manner, the SIFS 6 consists of four arms with two overlapping lazy-S shapes. In contrast, the SIFS 1 consists of two arms with a single lazy-S shape.

Figure 9:
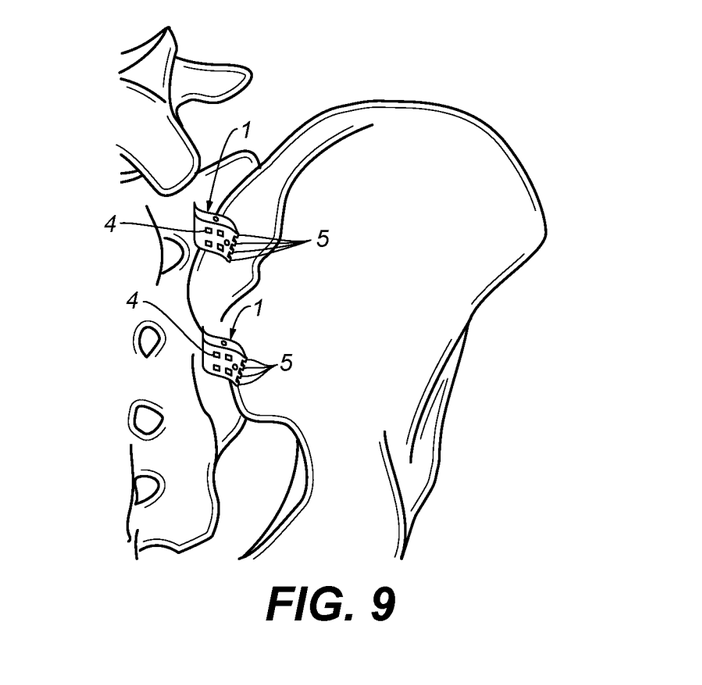
FIG. 9 demonstrates certain sites for placement of two SIFS units.
Figure 10:
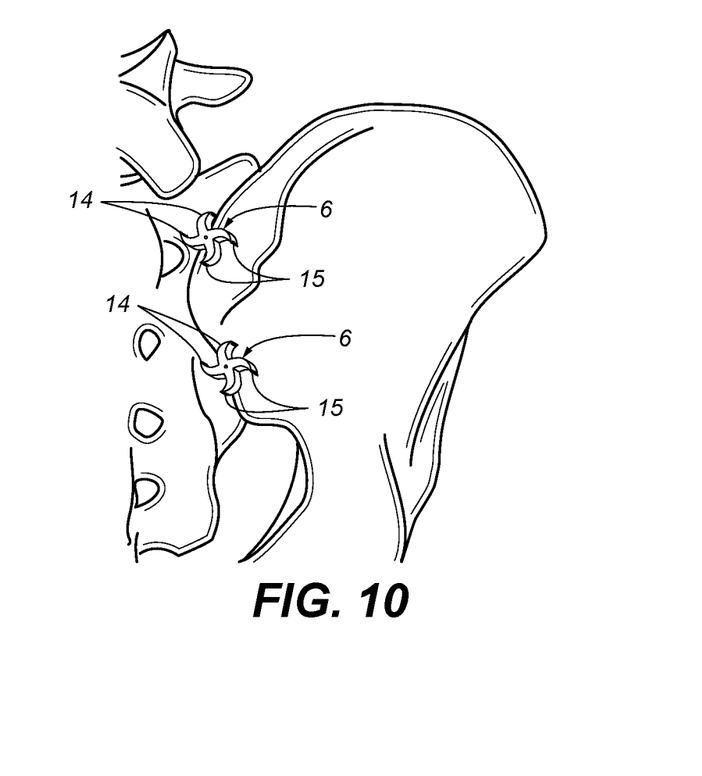
FIG. 10 shows implantation of an alternative embodiment.

In some embodiments, at least two SIFS devices are used to stabilize and fuse the SU and, in some instances, three SIFS may be used. This is a decision left to the judgment of the surgeon. In FIG. 9, a pair of SIFS 1 has been disposed over the respective guide needles and into the receiving bed. Likewise, FIG. 10 demonstrates an alternative embodiment of the SIFS 6 which has been provided with four arms and is secured into the sacroiliac joint with two arms 14 engaging the sacrum and two arms 15 engaging the ilium.

Figure 11:
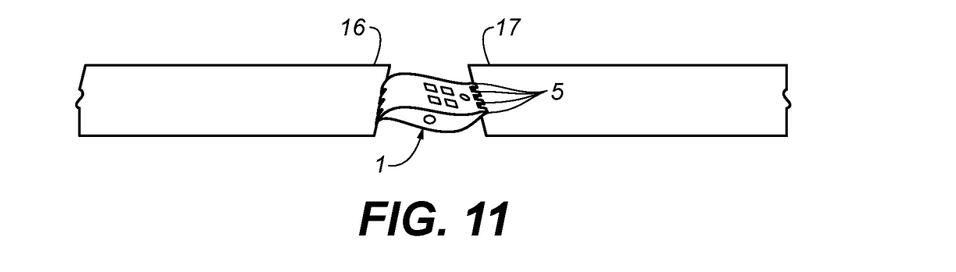
FIG. 11 shows a SIFS placed into a pseudoarthrosis of a long bone.
Figure 12:
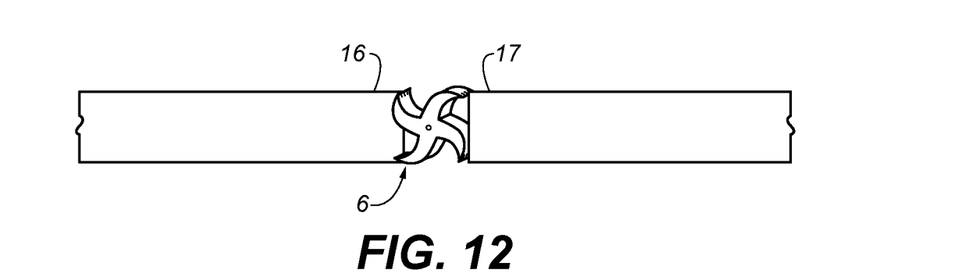
FIG. 12 depicts a view of a SIFS placed into the long bone.

As shown in FIG. 11 and FIG. 12, the SIFS could also be utilized to treat fracture sites which suffer from non-union. In these figures a non-union site is pictured with an SIFS having been placed in between the bone fracture fragments 16, 17. Because the projections 5 engage the bone, the site is stabilized, and bone fusion is promoted.

It is anticipated that all implanted components of the sacroiliac stabilizer may be fabricated from surgical titanium. However, stainless steel, molybdenum, other metal alloys such as chromium containing alloys, Nitinol, ceramic, porcelain, composite, polyesters, or any other substance known or acceptable to the art.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

As can be seen by FIG. 5a the length of the SIFS across the two arms, 500, 512 of the two arms is greater than the depth of the device along its turning axis 3. This provides a relatively flat disk device that sits in the pocket form across the joint of the sacrum and the iliac. When the SIF is rotated on quarter rotation at least one arm of the SIF engages the sacrum, and the second arm engages the ilium. Furthermore, the arm lengths 500, 512 are much greater than the arm width 508. By at least a factor of 3.

These dimensions provide a disk-shaped joining device as opposed to previous sacroiliac fusion devices that are more rod-like in form.

In specific embodiment the invention encompasses A sacroiliac fusion stabilizer (SIFS) for fusing a first bone fracture fragment to a second bone fracture fragment, the SIFS comprising: a joint fuser comprising a first blade and a second blade attached to a central rotatable axis with a center opening forming a cannulation; the first blade having a first face side surface and a second side surface being spaced from the second lateral surface by a depth that defines said first side and said second side; a cannulation that extends from the first side, through the SIFS and terminates at the second side; wherein said width is less than the dimension of the length of said first blade: wherein each of said first blade and said second blade have a t first curvature and the second curvature providing a lazy-S shape such that the first lateral surface contacts the second lateral surface at a first junction and a second junction, the first junction being disposed proximate the first lateral surface and the second junction being disposed proximate the second lateral surface and wherein the dimension of the SIFS from the outermost tip of said first arm to said second most tip The SIFS as previously described can furthermore have a plurality of projections on an outermost tip of the first blade, and the second blade has a plurality junction provides a second plurality of projections, wherein each projection in the first plurality of projections is spaced from a first lateral line by a first distance that is unique within the first plurality of projections, each projection in the second plurality of projections is spaced from a second lateral line by a second distance that is unique within the second plurality of projections.

The SIFS as recited in claim 2, wherein the SIFS consists of a first arm and a second arm, wherein the first junction is disposed at a terminus of the first arm and the second junction is disposed at a terminus of the second arm.

The SIFS consists of a first arm, a second arm, a third arm and a fourth arm, wherein the first junction is disposed at a terminus of the first arm and the second junction is disposed at a terminus of the second arm, the SIFS further comprising a third lateral surface having a third curvature; a fourth lateral surface, opposite the third lateral surface, having a fourth curvature, the third lateral surface being spaced from the fourth lateral surface by a depth that defines a third side and a fourth side, the third curvature and the fourth curvature providing a second lazy-S shape such that the third lateral surface contacts the fourth lateral surface at a third junction and a fourth junction, the third junction being disposed proximate the second lateral surface and the fourth junction being disposed proximate the fourth lateral surface, wherein the third junction is disposed at a terminus of the third arm and the fourth junction is disposed at a terminus of the fourth arm.

A sacroiliac fusion stabilizer (SIFS) for fusing a first bone fracture fragment to a second bone fracture fragment, the SIFS comprising at least a first arm and a second arm defined by a first lateral surface having a first curvature; a second lateral surface, opposite the first lateral surface, having a second curvature; the first lateral surface being spaced from the second lateral surface by a depth that defines a first side and a second side; a cannulation that extends from the first side, through the SIFS and terminates at the second side; the first curvature and the second curvature providing a lazy-S shape such that the first lateral surface contacts the second lateral surface at a first junction and a second junction, the first junction being disposed proximate the first lateral surface to form the first arm and the second junction being disposed proximate the second lateral surface to form the second arm: the first junction providing a first plurality of projections, and the second junction providing a second plurality of projections, wherein each projection in the first plurality of projections is spaced from a first lateral line by a first distance that is unique within the first plurality of projections; each projection in the second plurality of projections is spaced from a second lateral line by a second distance that is unique within the second plurality of projections. And wherein the cannula length is no greater than ⅕th the length of the SIFS width defined as stretching from the first blade tip to the second blade tip.

What is claimed is:

1. A sacroiliac fusion stabilizer (SIFS) for fusing a first bone fracture fragment to a second bone fracture fragment, the SIFS comprising:
    a joint fuser comprising a first blade and a second blade attached to a central rotatable axis with a center opening forming a cannulation;
    the first blade having a first face side surface and said second blade having a second face side surface being spaced from the second lateral surface by a depth that defines said first face side and said second face side;
    said cannulation that extends from the first side, through the SIFS and terminates at the second side to form the width of said (SIFS); wherein said width is less than the dimension of the length of said first blade; wherein each of said first blade and said second blade have a first curvature and a second curvature the second curvature providing a lazy-S shape such that the first blade contacts the second blade at a first junction and a second junction, the first junction being disposed proximate first lateral surface and the second junction being disposed proximate a second lateral surface and wherein the dimension of the SIFS from the outermost tip of said first arm to said cannulation is greater than the length of said second arm from the cannulation to the tip of said second arm.

2. The SIFS as recited in claim 1, wherein the first blade has a plurality of projections on an outermost tip, and the second blade has a plurality junction provides a second plurality of projections, wherein
    each projection in the first plurality of projections is spaced from a first lateral line by a first distance that is unique within the first plurality of projections;
    each projection in the second plurality of projections is spaced from a second lateral line by a second distance that is unique within the second plurality of projections.

3. The SIFS as recited in claim 2, wherein the SIFS consists of a first arm and a second arm, wherein the first junction is disposed at a terminus of the first arm and the second junction is disposed at a terminus of the second arm.

4. The SIFS as recited in claim 2, wherein the SIFS consists of a first arm, a second arm, a third arm and a fourth arm, wherein the first junction is disposed at a terminus of the first arm and the second junction is disposed at a terminus of the second arm, the SIFS further comprising:
    a third lateral surface having a third curvature;
    a fourth lateral surface, opposite the third lateral surface, having a fourth curvature;

the third lateral surface being spaced from the fourth lateral surface by a depth that defines a third side and a fourth side;

the third curvature and the fourth curvature providing a second lazy-S shape such that the third lateral surface contacts the fourth lateral surface at a third junction and a fourth junction, the third junction being disposed proximate the second lateral surface and the fourth junction being disposed proximate the fourth lateral surface, wherein the third junction is disposed at a terminus of the third arm and the fourth junction is disposed at a terminus of the fourth arm.

5. A device for fusing a first bone fracture fragment to a second bone fracture fragment, the SIFS comprising at least a first arm and a second arm defined by:

a first lateral surface having a first curvature;

a second lateral surface, opposite the first lateral surface, having a second curvature;

the first lateral surface being spaced from the second lateral surface by a depth that defines a first side and a second side;

a cannulation that extends from the first side, through the SIFS and terminates at the second side;

the first curvature and the second curvature providing a lazy-S shape such that the first lateral surface contacts the second lateral surface at a first junction and a second junction, the first junction being disposed proximate the first lateral surface to form the first arm and the second junction being disposed proximate the second lateral surface to form the second arm;

the first junction providing a first plurality of projections, and the second junction providing a second plurality of projections, wherein each projection in the first plurality of projections is spaced from a first lateral line by a first distance that is unique within the first plurality of projections;

each projection in the second plurality of projections is spaced from a second lateral line by a second distance that is unique within the second plurality of projections.

6. The SIFS as recited in claim 5, wherein the SIFS consists of the first arm and the second arm.

7. The SIFS as recited in claim 5, wherein the SIFS further comprise a third arm and a fourth arm, the third arm and the fourth arm defining a second lazy-S.

* * * * *